US006284257B1

(12) United States Patent
Khayat et al.

(10) Patent No.: US 6,284,257 B1
(45) Date of Patent: Sep. 4, 2001

(54) COSMETIC WATER EMULSION CONTAINING AT LEAST ONE VEGETABLE OIL

(75) Inventors: Carine Khayat, La Varenne; Didier Candau, Bievres, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 08/258,024

(22) Filed: Jun. 10, 1994

(30) Foreign Application Priority Data

Jun. 10, 1993 (FR) .................................................. 93 07003

(51) Int. Cl.$^7$ ....................................................... A61K 7/48
(52) U.S. Cl. ............................ 424/401; 424/59; 514/854; 514/846; 514/847; 514/937; 514/938
(58) Field of Search ..................... 424/401, 59; 514/937, 514/938, 845–847

(56) References Cited

U.S. PATENT DOCUMENTS 4,976,953 * 12/1990 Orr ......................................... 424/47
5,310,556 * 5/1994 Ziegler ................................. 424/401

FOREIGN PATENT DOCUMENTS

9206778 * 4/1992 (WO) .

* cited by examiner

Primary Examiner—Thurman K. Page
(74) Attorney, Agent, or Firm—Nixon & Vanderhye P.C.

(57) ABSTRACT

A cosmetic or dermatological composition in the form of a stable oil-in-water emulsion comprises (a) from 15 to 50 percent by weight of at least one vegetable oil containing at least 40 percent linoleic acid triglyceride, (b) from 2 to 7 percent by weight of a self-emulsifiable composition comprising from 60 to 90 percent by weight of at least one fatty alcohol having from 12 to 22 carbon atoms, from 10 to 40 percent by weight of at least one alkylpolysaccharide wherein the alkyl moiety has from 12 to 22 carbon atoms, and from 0 to 5 percent by weight of polysaccharide, (c) from 0.5 to 5 percent by weight of a coemulsifying agent selected from the group consisting of at least one saturated fatty alcohol having from 16 to 32 carbon atoms, a saturated fatty acid having from 16 to 32 carbon atoms and a mixture thereof, (d) from 0.1 to 1 percent by weight of a gelling agent, the remainder consisting essentially of an aqueous phase.

10 Claims, No Drawings

COSMETIC WATER EMULSION CONTAINING AT LEAST ONE VEGETABLE OIL

The subject of the present invention is a composition in the form of a stable oil-in-water (O/W) emulsion consisting essentially of at least one vegetable oil with a high linoleic acid content, of a surface-active agent based on fatty alcohols and of a gelling agent, and its use in various cosmetic and dermatological applications.

Vegetable oils, such as sweet almond oil or hazelnut oil, are known for their cosmetic properties but their uses in the preparation of emulsions, however, present serious difficulties, especially as regards their stability. In order to solve this problem and to avoid the use of more or less irritating surface-active agents, the use was proposed, in Application WO 92/06778, of a self-emulsifiable composition based on fatty alcohols and alkylpolysaccharides.

However, the oils described in this patent are oils containing a low percentage of linoleic acid triglycerides. Now, this acid, as an unsaturated fatty acid, plays a very significant role in maintaining the lipid structures of the intercellular spaces of the stratum corneum as well as in the restoration of the barrier function of dry skins. Insofar as linoleic acid is not synthesized by the human body, it must therefore be supplied to the cutaneous tissue topically or optionally orally in the free acid form or triglyceride form.

It was thus desirable to be able to obtain stable emulsions from vegetable oils which are particularly rich in linoleic acid.

The use of the self-emulsifiable composition, according to WO 92/06778, does not, however, make it possible to obtain, with oils of this type, emulsions which are sufficiently stable with time.

It has now been surprisingly and unexpectedly observed that, by combining these vegetable oils with the self-emulsifiable composition according to Patent WO 92/06778, in the presence of a coemulsifying agent and of a gelling agent, it was possible to obtain fine and stable emulsions, that is to say not showing dephasing after two months at 45° C.

The good stability of the (O/W) emulsions according to the invention could be obtained especially by virtue of the presence of the gelling agent, used in a well-defined proportion and chosen from natural gelling agents.

The subject of the present invention is thus a cosmetic or dermatological composition in the form of a stable oil-in-water emulsion, characterized in that it contains:

(a) from 15 to 50% by weight of at least one vegetable oil consisting of at least 40% linoleic acid triglycerides, (b) from 2 to 7% by weight of a self-emulsifiable composition or combination comprising from 60 to 90% by weight of at least one fatty alcohol having from 12 to 22 carbon atoms, from 10 to 40% by weight of at least one alkylpolysaccharide whose alkyl chain has from 12 to 22 carbon atoms, and from 0 to 5% by weight of polysaccharide, (c) from 0.5 to 5% by weight of a coemulsifying agent chosen from at least one saturated fatty alcohol having from 16 to 32 carbon atoms, a saturated fatty acid having from 16 to 32 carbon atoms and their mixtures, (d) from 0.1 to 1% by weight of a gelling agent, and the remainder consisting essentially of an aqueous phase.

According to a preferred embodiment, the ratio by weight of the vegetable oil to the alkylpolysaccharide of the self-emulsifiable combination is greater than or equal to 10.

Mention may be made, among vegetable oils comprising at least 40% linoleic acid triglycerides which can be used according to the invention, of wheat germ oil, maize germ oil, soybean oil, sunflower oil, cottonseed oil, lucerne oil, poppy oil, red kuri oil, sesame oil, rapeseed oil, evening primrose oil, millet oil, barley oil, quinoa oil, rye oil, safflower oil, candlenut oil and passionflower oil.

The percentages of triglycerides of palmitic, oleic and linoleic acids constituting these vegetable oils are respectively between approximately 0 and 10%, 20 and 30%, and 40 and 70%.

According to a preferred embodiment of the invention, the proportion of vegetable-oils is between 15 and 40% by weight with respect to the total weight of the emulsion.

Mention may be made, among the self-emulsifiable combinations or compositions described in WO 92/06778, of in particular the product marketed under the name of. "Montanov 68®" by the Company Seppic, which consists essentially of the combination of approximately 77% cetyl/stearyl alcohol ($C_{16}$–$C_{18}$) and approximately 23% cetearylglucosides.

According to a specific embodiment of the invention, the alkyl radical of the alkylpolysaccharide is identical to that of the fatty alcohol of the self-emulsifiable composition.

According to a preferred embodiment of the invention, the proportion of self-emulsifiable composition is between 2 and 6% by weight with respect to the total weight of the emulsion.

Mention may be made, among the fatty alcohols having from 16 to 32 carbon atoms used as coemulsifying agents, of cetyl alcohol, stearyl alcohol, their mixtures and a mixture of octacosanol and fatty alcohols having from 24 to 32 carbon atoms.

Mention may be made, among the fatty acids having from 16 to 32 carbon atoms used as coemulsifying agents, of palmitic acid and stearic acid.

Use may be made according to the invention, as coemulsifying agent belonging to the group of fatty acids having from 16 to 32 carbon atoms, of a product of natural origin, namely sumach wax, which contains approximately 40% $C_{16}$ fatty acids and 50% $C_{18}$ fatty acids.

According to a preferred embodiment, the proportion of coemulsifying agent is between 0.5 and 3% by weight with respect to the total weight of the emulsion.

Mention may be made, among gelling agents which can be used according to the invention, of seed flours such as guar gum and carob bean gum, tree exudates such as gum arabic, karaya gum, tragacanth gum and ghatti gum, marine algae extracts such as carraghenates, alginates and agar-agar, microorganism exudates such as xanthan gum, cellulose derivatives and mixtures of these. Among these gelling agents, xanthan gums and alginates, especially propylene glycol alginate, are particularly preferred.

The emulsions according to the invention can additionally contain, with a view to increasing their cosmetic qualities, a cosmetic wax such as, for example, rice wax, candelilla wax or Japan wax, these waxes having a melting point between 46 and 52° C. The proportion of wax is generally between 0.5 and 3%, and preferably between 1 and 2%, by weight with respect to the total weight of the emulsion.

The emulsions according to the invention can also contain at least one conventional adjuvant. Mention may be made, among the latter, of in particular UV screening agents, vitamins, essential oils, plant proteins, anti-oxidizing agents, preserving agents, fragrances, ceramides, moisturizing agents, lubricating agents, polysaccharides, fillers and various active principles.

The compositions according to the invention in the form of (O/W) emulsions can be used in various cosmetic or dermatological applications, for example in the form of creams for the face or for the body, of make-up removal milks, of body milks or of face masks. These compositions can also be used for make-up after addition of pigments, especially in the form of foundation creams.

They can also be used as suncreams after addition of UV-B and/or UV-A screening agents.

A number of examples of compositions according to the invention in the form of oil-in-water emulsions will now be given by way of illustration.

COMPOSITION EXAMPLES

Example 1

Moisturizing cream

| Fatty phase A | |
| --- | --- |
| Mixture (A1) | |
| Self-emulsifiable composition marketed under the name MONTANOV 68 ® by the Company Seppic | 2.5 g |
| Cetyl alcohol | 1 g |
| Sumach wax | 1.5 g |
| Mixture (A2) | |
| Maize germ oil | 24 g |
| Anti-oxidizing agent | q.s. |
| Aqueous phase B | |
| Xanthan gum | 0.2 g |
| Preserving agents | q.s. |
| Water | 25 g |

Fatty phase A is prepared in the following way:

Mixture (A1) and Mixture (A2) are heated separately to 80° C. and 70° C. respectively with magnetic stirring, Mixture (A1) is then poured into Mixture (A2) and homogenization is carried out.

Aqueous phase B is prepared in the following way:

Water is heated to 80° C., the preserving agents are dissolved therein and then the gelling agent is introduced with magnetic stirring until an opaque homogeneous gel is obtained. The mixture is then cooled to 70° C.

Phase A is then slowly poured into Phase B, with stirring, at 70° C., over approximately 5 minutes and the mixture is then allowed to cool to 30° C. An amount of water is then added to the mixture obtained above which is sufficient for 100 g and stirring is carried out until a homogeneous cream is obtained.

The cream obtained is very soft, smooth, pleasant to the touch and leaves the skin matt after application. Its viscosity is between 6 and $10 \times 10^{-1}$ Pa·s (6 and 10 poises).

It has excellent stability on centrifuging at 3000 revs/min for one hour and after storing for 2 months at 45° C.

Example 2

Moisturizing milk

| Fatty phase A | |
| --- | --- |
| Mixture (A1) | |
| Self-emulsifiable composition marketed under the name MONTANOV 68 ® by the Company Seppic | 2.3 g |
| Stearyl alcohol | 1 g |

| -continued | |
| --- | --- |
| Mixture (A2) | |
| Soybean oil | 16.7 g |
| Anti-oxidizing agent | q.s. |
| Aqueous phase B | |
| Xanthan gum | 0.6 g |
| Preserving agents | q.s. |
| Water | 25 g |

This moisturizing milk is obtained according to the same procedure as that described in Example 1 by mixing the above Phases A and B and addition of a sufficient amount of water for 100 g.

It is very easy to apply to the face and to the body and is moreover very soft on application.

Its viscosity is between 210 and 290 cps and shows the same stability criteria as those described for the cream of Example 1.

Example 3

Cleansing cream

| Fatty phase A | |
| --- | --- |
| Mixture (A1) | |
| Self-emulsifiable composition marketed under the name MONTANOV 68 ® by the Company Seppic | 4.25 g |
| Cetyl alcohol | 0.75 g |
| Japan wax | 0.5 g |
| Mixture (A2) | |
| Maize germ oil | 20 g |
| Wheat germ oil | 5 g |
| Aqueous phase B | |
| Propylene glycol alginate | 0.6 g |
| Preserving agents | q.s. |
| Water | 25 g |

This cream is prepared according to the same procedure as that described in Example 1. When the temperature has fallen again to 30° C., an amount of water sufficient for 95 g, and then 5 g of kaolin, are added to the mixture with stirring and then the mixture is homogenized.

The cleansing cream obtained is white, has a good cleansing power and is very soft, on application and after application. Its viscosity is between 15 and 25 poises. This cream has excellent stability on centrifuging at 3000 revs/min for one hour and after storing for 2 months at any temperature.

Example 4

Cleansing milk

| Fatty phase A | |
| --- | --- |
| Mixture (A1) | |
| Self-emulsifiable composition marketed under the name MONTANOV 68 ® by the Company Seppic | 2.45 g |
| Stearic acid | 1 g |
| Palmitic acid | 0.8 g |
| Mixture (A2) | |
| Maize germ oil | 24 g |
| Anti-oxidizing agents | q.s. |

-continued

| Aqueous phase B | |
|---|---|
| Xanthan gum | 0.2 g |
| Wheat protein | 0.5 g |
| Preserving agents | q.s. |
| Water | 25 g |

This cleansing milk is obtained according to the same procedure as that described in Example 1 by mixing the above Phases A and B and addition of a sufficient amount of water for 100 g.

It is very soft on application.

Its viscosity is between 220 and $290 \times 10^{-3}$ Pa·s (220 and 290 cP) and shows the same stability criteria as those described for the cream of Example 1.

We claim:

1. A cosmetic or dermatological composition in the form of a stable oil-in-water emulsion, comprising
    (a) from 15 to 50% by weight of at least one vegetable oil containing at least 40% linoleic acid triglycerides,
    (b) from 2 to 7% by weight of a self-emulsifiable composition comprising from 60 to 90% by weight of at least one fatty alcohol having from 12 to 22 carbon atoms, from 10 to 40% by weight of at least one alkylpolysaccharide whose alkyl chain has from 12 to 22 carbon atoms, and from 0 to 5% by weight of polysaccharide,
    (c) from 0.5 to 5% by weight of a coemulsifying agent selected from the group consisting of at least one saturated fatty alcohol having from 16 to 32 carbon atoms, a saturated fatty acid having from 16 to 32 carbon atoms and a mixture thereof,
    (d) from 0.1 to 1% by weight of a natural gelling agent selected from the group consisting of a seed flour, a tree exudate, a marine algae exudate, a marine algae extract, and a microorganism exudate, and the remainder consisting essentially of an aqueous phase.

2. The composition of claim 1 wherein the ratio by weight of said vegetable oil to said alkylpolysaccharide of said self-emulsifiable composition is greater than or equal to 10.

3. The composition of claim 1, wherein said fatty alcohol having from 12 to 22 carbon atoms of said self-emulsifiable composition is cetyl/stearyl alcohol ($C_{16}$–$C_{18}$) and said alkylpolysaccharide is cetearylglucoside.

4. The composition of claim 1 wherein said vegetable oil is selected from the group consisting of: wheat germ oil, maize germ oil, soybean oil, sunflower oil, cottonseed oil, lucerne oil, poppy oil, red kuri oil, sesame oil, rapeseed oil, evening primrose oil, millet oil, barley oil, quinoa oil, rye oil, safflower oil, candlenut oil and passionflower oil.

5. The composition of claim 1 wherein said vegetable oil is present in an amount ranging from 15 to 40% by weight based on the total weight of said oil-in-water emulsion.

6. The composition of claim 1 wherein said self-emulsifiable composition is present in an amount ranging from 2 to 6% by weight based on the total weight of said oil-in-water emulsion.

7. The composition of claim 1 wherein said coemulsifying agent is selected from the group consisting of: cetyl alcohol, stearyl alcohol, a mixture of cetyl alcohol an d stearyl alcohol, a mixture of octacosanol and a fatty alcohol having from 24 to 32 carbon atoms, palmitic acid and stearic acid.

8. The composition of claim 1 wherein said coemulsifying agent is present in an amount ranging from 0.5 to 3% by weight based on the total weight of said oil-in-water emulsion.

9. The composition of claim 1 which also includes from 0.5 to 3% by weight, based on the total weight of said oil-in-water emulsion, of at least one cosmetic wax selected from the group consisting of: rice wax, candelilla wax and Japan wax.

10. The composition of claim 1 which also includes at least one adjuvant selected from the group consisting of a screening agent, a vitamin, an essential oil, a plant protein, an anti-oxidizing agent, a preserving agent, a fragrance, a ceramide, a moisturizing agent, a lubricating agent, a polysaccharide, and a filler.

* * * * *